(12) United States Patent
Geitz

(10) Patent No.: US 8,142,514 B2
(45) Date of Patent: *Mar. 27, 2012

(54) INTRAGASTRIC PROSTHESIS FOR THE TREATMENT OF MORBID OBESITY

(75) Inventor: Kurt Geitz, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,977

(22) Filed: Aug. 30, 2010

(65) Prior Publication Data

US 2010/0324696 A1   Dec. 23, 2010

Related U.S. Application Data

(63) Continuation of application No. 11/503,538, filed on Aug. 10, 2006, now Pat. No. 7,799,088, which is a continuation of application No. 10/795,491, filed on Mar. 8, 2004, now Pat. No. 7,090,699, which is a continuation of application No. 10/057,469, filed on Jan. 25, 2002, now Pat. No. 6,755,869, which is a continuation of application No. 10/007,819, filed on Oct. 9, 2001, now abandoned.

(51) Int. Cl.
*A61F 2/04* (2006.01)
(52) U.S. Cl. ..................................... 623/23.65
(58) Field of Classification Search .................. 600/30, 600/37; 604/93.01, 96.01, 103.06, 103.07, 604/103.1, 104, 107; 606/191, 198; 623/23.64–23.67, 23.7, 23.75
See application file for complete search history.

(56) References Cited

U.S. PATENT DOCUMENTS

| | | | | |
|---|---|---|---|---|
| 6,755,869 B2 * | 6/2004 | Geitz | ......................... | 623/23.65 |
| 7,799,088 B2 * | 9/2010 | Geitz | ......................... | 623/23.65 |

* cited by examiner

*Primary Examiner* — William H. Matthews
(74) *Attorney, Agent, or Firm* — Fay Kaplun & Marcin, LLP

(57) ABSTRACT

A porous weave of bioabsorbable filaments having an open mesh configuration is formed into an oblate shape having dimensions greater than the esophageal opening and gastric outlet of a stomach. The resulting prosthesis is deployed in the stomach and is of a size to be retained in the proximate portion thereof for exerting pressure on the upper fundus. The prosthesis limits the amount of food that may be held within the stomach, and exerts pressure on the fundus to create a sensation of being full, resulting in weight loss.

17 Claims, 2 Drawing Sheets

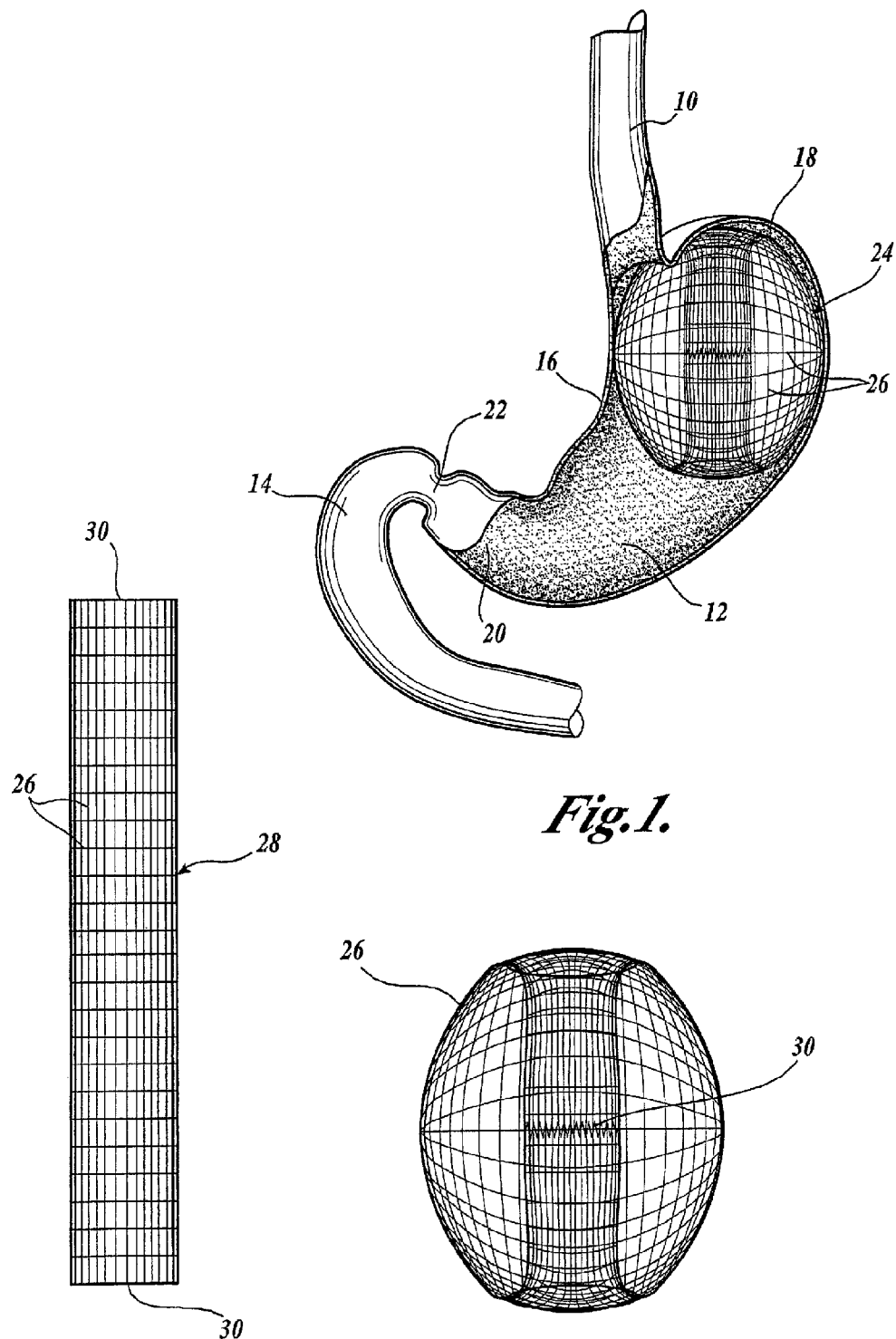

INTRAGASTRIC PROSTHESIS FOR THE TREATMENT OF MORBID OBESITY

PRIORITY CLAIM

The present application is a Continuation of U.S. patent application Ser. No. 11/503,538 filed on Aug. 10, 2006 now U.S. Pat. No. 7,799,088; which is a Continuation application of U.S. patent application Ser. No. 10/795,491 filed on Mar. 8, 2004 now U.S. Pat. No. 7,090,699 issued on Aug. 15, 2006; which is a Continuation application of U.S. patent application Ser. No. 10/057,469 filed on Jan. 25 2002 now U.S. Pat. No. 6,755,869 issued on Jun. 29, 2004; which is a Continuation application of abandoned U.S. patent application Ser. No. 10/007,819 filed on Nov. 9, 2001, the entire disclosure of these applications is expressly incorporated herein by reference.

FIELD OF INVENTION

The present invention pertains to a resilient, flexible, compressible, bio-compatible prosthesis insertable into the stomach to effect weight loss over a controlled period.

BACKGROUND

The incidence of obesity and its associated health-related problems have reached epidemic proportions in the United States. See, for example, P. C. Mun et al., "Current Status of Medical and Surgical Therapy for Obesity" *Gastroenterology* 120:669-681(2001). Recent investigations suggest that the causes of obesity involve a complex interplay of genetic, environmental, psycho-behavioral, endocrine, metabolic, cultural, and socio-economic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea.

Estimates of the incidence of morbid obesity are approximately 2% of the U.S. population and 0.5% worldwide. Current treatments range from diet, exercise, behavioral modification, and pharmacotherapy to various types of surgery, with varying risks and efficacy. In general, nonsurgical modalities, although less invasive, achieve only relatively short-term and limited weight loss in most patients. Surgical treatments include gastroplasty to restrict the capacity of the stomach to hold large amounts of food, such as by stapling or "gastric banding." Other surgical procedures include gastric bypass and gastric "balloons" which, when deflated, may be inserted into the stomach and then are distended by filling with saline solution.

The need exists for cost effective, less invasive interventions for the treatment of morbid obesity.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a novel system for treatment of morbid obesity by use of a bioabsorbable gastric prosthesis placed in the stomach through a minimally invasive procedure. The prosthesis takes up space in the stomach so that the stomach can hold a limited amount of food, and preferably exerts pressure on the upper fundus to create a sensation of being full. The material of the prosthesis can be selected to degrade over a predetermined period and pass out of the patient without additional intervention.

In the preferred embodiment, the prosthesis is a porous weave of bioabsorbable filaments having an open mesh configuration. The prosthesis can be formed from a cylindrical stent, such as by reverting the ends of the cylinder and joining them at the center. The filaments preferably have memory characteristics tending to maintain an oblate shape with sufficient resiliency and softness so as not to unduly interfere with normal flexing of the stomach or cause abrasion of the mucus coat constituting the inner lining of the stomach. The prosthesis may be free floating in the stomach, but is shaped so as to be biased against the upper fundus, or it may be tacked in position adjacent to the fundus by bioabsorbable sutures.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a somewhat diagrammatic elevation of a stomach and adjacent parts of the alimentary canal, with the wall adjacent to the viewer partially broken away to reveal an intragastric prosthesis in accordance with the present invention;

FIG. 2 is a side elevation of a cylindrical stent from which a prosthesis in accordance with the present invention may be formed;

FIG. 3 is a side elevation of a prosthesis in accordance with the present invention, formed from the stent of FIG. 2.

DETAILED DESCRIPTION

Figure 4:
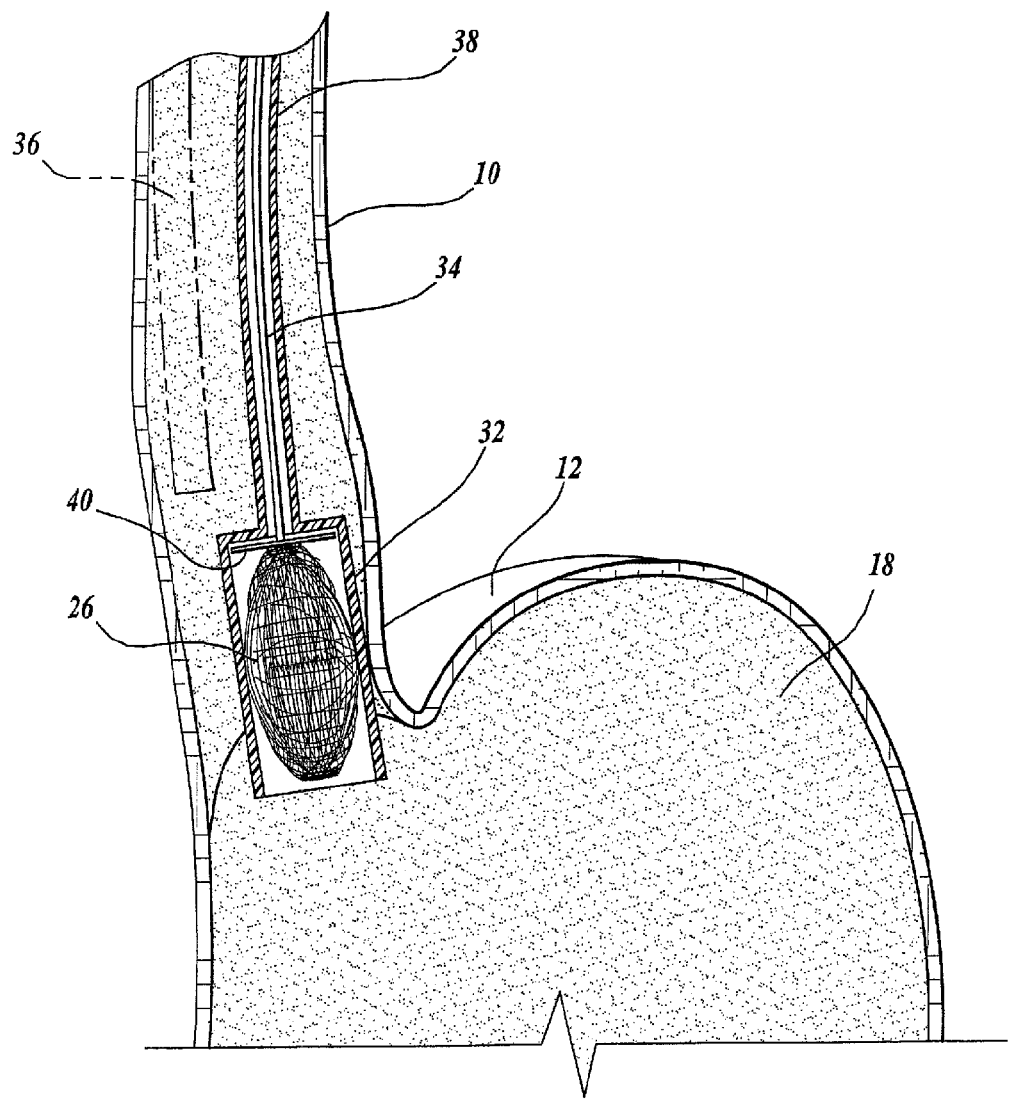
FIG. 4 is a diagrammatic elevation corresponding to FIG. 1, illustrating insertion of a prosthesis in accordance with the present invention through the esophagus and into the stomach.

The present invention provides a volume-filling prosthesis insertable into the stomach for treatment of morbid obesity by taking up space in the stomach to reduce its capacity and by exerting pressure to create a sensation of being full, particularly on the upper fundus.

FIG. 1 illustrates a central portion of the alimentary canal including the distal segment of the esophagus 10, the stomach 12, and the duodenum 14 (proximate segment of the small intestine). The esophagus 10 opens into the stomach 12 toward the top of the lesser curvature 16 adjacent to the fundus 18. The pyloric part 20 of the stomach leads to the duodenum by way of the gastric outlet or pylorus 22 which forms the distal aperture of the stomach and has an enclosing circular layer of muscle which is normally contracted to close the aperture but which relaxes to provide an open but restricted passage. Although subject to substantial variation in different individuals, representative dimensions for the stomach are approximately 8 cm long (fundus to pylorus) by 5 cm wide (greatest distance between lesser and greater curvatures), with the esophageal opening being approximately 2 cm in diameter and the pylorus having a maximum open diameter of about 2 cm.

In accordance with the present invention, an oblate, volume-filling prosthesis 24 is held within the stomach, sized for reception in the proximate portion adjacent to the opening of the esophagus and fundus. Such prosthesis preferably is a porous body formed of a loose weave of thin polymer filaments 26, having large spaces between filaments for an open area of at least about 80%, preferably more than 90%, so as not to impede the flow of gastric juices or other functioning in the stomach. The filaments 26 have substantial memory characteristics for maintaining the desired oblate shape and size. However, the filaments preferably are sufficiently soft and flexible to avoid abrasion of the mucus coat forming the inner lining of the stomach and to enable normal flexing and shape changes. The size of the prosthesis 24 is substantially greater than the opening of the esophagus, at least about 3 cm in the narrowest dimension, preferably at least about 4 cm. The longer dimension of the oblate prosthesis is greater than 4 cm, preferably at least about 5 cm to prevent the prosthesis from free movement within the stomach. The size and shape of the prosthesis tend to maintain it in the position indicated in FIG. 1, adjacent to the fundus 18 and remote from the pyloric part 20. Thus, while the prosthesis occupies a substantial portion of the volume of the stomach, preferably approximately one-half the volume, the prosthesis does not interfere with normal digestion of food, such as by gastric juices (hydrochloric acid and digestive enzymes) nor with passage of food through the pyloric part 20 and its opening 22 to the duodenum 14.

With reference to FIG. 2, the prosthesis can be formed from a substantially cylindrical stent 28 having the desired porous weave and large open area. The filaments 26 and weave pattern are selected to achieve memory characteristics biasing the prosthesis to the cylindrical condition shown. In the preferred embodiment, the opposite ends 30 of the stent are reverted, the end portions are rolled inward, and the ends are secured together such as by suturing. Alternatively, a disk of the same pattern and material can be used in securing the reverted ends together. The resiliency of the filaments tends to bulge the resulting prosthesis 26 outward to the desired oblate shape.

Prior to reversion of the ends, stent 28 in the condition shown in FIG. 2 can be approximately 2-3 cm in diameter and approximately 8-10 cm long, in a representative embodiment. The filaments can have a diameter of about 0.010 inch to about 0.25 inch. The filaments may be coated or impregnated with other treating agents, such as appetite suppressants, or agents to decrease the likelihood of gastric problems, such as ulcers, due to the presence of a foreign object. However, such problems are unlikely due to the biocompatible nature and the resilient flexibility of the prosthesis.

It is preferred that the filaments 26 be formed of a bioabsorbable polymer such as a polyglycolic acid polymer or polylactic acid polymer. Similar materials are used for some bioabsorbable sutures having "forgiving" memory characteristics and sufficient "softness" that tissue abrasion is inhibited. The absorption characteristics of the filaments 26 can be selected to achieve disintegration of the prosthesis 26 within the range of three months to two years, depending on the severity of obesity. In the preferred embodiment, the prosthesis will absorb and pass naturally from the stomach approximately 6 months after deployment.

Non-bioabsorbable materials may be used, such as Nitinol, which exhibit the desired springiness but which would require that the prosthesis be retrieved. An advantage of the preferred, bioabsorbable embodiment of the invention is that delivery can be through the esophagus, with no additional intervention being required.

With reference to FIG. 4, preferably from the condition shown in FIG. 3, the prosthesis 26 can be compressed to a generally cylindrical shape having a diameter of no more than about 2 cm such that the compressed prosthesis can be carried in a short (approximately 5 cm to 6 cm long) loading tube 32.

The loading tube can be advanced along the esophagus by a central tube 34 of smaller diameter, under the visualization allowed by a conventional endoscope 36. The tube 34 can enclose a core wire 38 to actuate a pusher mechanism 40 for ejecting the prosthesis 26 when the opening of the esophagus into the stomach has been reached. The endoscope and deployment mechanism can then be retracted.

While the preferred embodiment of the invention has been illustrated and described, it will be appreciated that various changes can be made therein without departing from the spirit and scope of the invention. For example, while it is preferred that the prosthesis be sized for self-retention in the desired position in the stomach, it also may be secured in position by a few sutures applied endoscopically, preferably in or adjacent to the fundus area of the stomach.

The invention claimed is:

1. A device for treatment of obesity, comprising:
   a prosthesis configured and dimensioned for insertion through an esophagus and having a porous body formed of a weave of filaments biased to a substantially cylindrical configuration;
   wherein opposing first and second ends of the prosthesis are reverted and secured to one another, the porous body being movable from a first insertion configuration wherein the porous body is configured for insertion through an esophagus to a second deployed configuration; and
   wherein dimensions of the porous body in the second deployed configuration are greater than dimensions of an esophageal opening.

2. The device of claim 1, wherein the first and second ends are secured to one another by sutures.

3. The device of claim 2, wherein the filaments are formed of a resilient polymer.

4. The device of claim 3, wherein the filaments and sutures are bioabsorbable.

5. The device of claim 1, further comprising:
   a loading tube configured to receive the porous body therewithin in the first insertion configuration during insertion through the esophagus;
   an advancing tube configured and dimensioned to advance the loading tube through the esophagus; and
   a deployment element configured to eject the porous body from the loading tube and into the stomach so that the porous body assumes the second deployed configuration.

6. The device of claim 1, wherein spaces provided between adjacent filaments compose approximately 80-90% of the outer surface of the porous body.

7. The device of claim 1, wherein the filaments are formed of non-bioabsorbable materials.

8. The device of claim 1, wherein the porous body is configured and dimensioned so that, when in the second deployed configuration, the porous body is held adjacent to a fundus of a stomach.

9. The device of claim 1, wherein the filaments are coated or impregnated with a medical treating agent.

10. A device for treatment of obesity, comprising:
    a prosthesis configured and dimensioned for insertion through an esophagus and having a porous body formed of a weave of filaments biased to a substantially cylindrical configuration;
    wherein opposing first and second ends of the prosthesis are reverted and secured to one another, the porous body being movable from a first insertion configuration to a second insertion configuration; and wherein the porous body is configured for insertion while in the first insertion configuration through an esophagus wherein dimensions of the porous body in the second insertion configuration are greater than dimensions of a gastric outlet.

11. The device of claim 10, wherein the porous body is configured to prevent interference with a passage of fluids and solids through the stomach and to the gastric outlet.

12. The device of claim 10, wherein the first and second ends are secured to one another by sutures.

13. The device of claim 12, wherein the filaments and sutures are formed of one of a bioabsorbable and a non-bioabsorbable resilient polymer.

14. The device of claim 10, further comprising:
a loading tube configured to receive the porous body therewithin in the first insertion configuration during insertion through the esophagus;
an advancing tube configured and dimensioned to advance the loading tube through the esophagus; and
a deployment element configured to eject the porous body from the loading tube and into the stomach so that the porous body assumes the second deployed configuration.

15. The device of claim 10, wherein spaces provided between adjacent filaments compose approximately 80-90% of the outer surface of the porous body.

16. The device of claim 10, wherein the porous body is configured and dimensioned so that, when in the second deployed configuration, the porous body is held adjacent to a fundus of a stomach.

17. The device of claim 10, wherein the filaments are coated or impregnated with a medical treating agent.

* * * * *

UNITED STATES PATENT AND TRADEMARK OFFICE
CERTIFICATE OF CORRECTION

| | | |
|---|---|---|
| PATENT NO. | : 8,142,514 B2 | Page 1 of 1 |
| APPLICATION NO. | : 12/870977 | |
| DATED | : March 27, 2012 | |
| INVENTOR(S) | : Geitz | |

It is certified that error appears in the above-identified patent and that said Letters Patent is hereby corrected as shown below:

In the Title Page, item (63): insert the following information:

--Related U.S. Application Data

Continuation of U.S. Patent Application Serial No. 11/503,538 filed on August 10, 2006; now U.S. Patent No. 7,799,088, which is a Continuation of U.S. Patent Application Serial No. 10/795,491, filed on March 8, 2004, now U.S. Patent No. 7,090,699, which is a Continuation of U.S. Patent Application Serial No. 10/057,469, filed on January 25, 2002, now U.S. Patent No. 6,755,869, which is a Continuation of U.S. Patent Application Serial No. 10/007,819, filed on November 9, 2001, now abandoned.--

Signed and Sealed this
Eighteenth Day of September, 2012

David J. Kappos
*Director of the United States Patent and Trademark Office*